United States Patent
Shimuta

(10) Patent No.: US 11,419,549 B2
(45) Date of Patent: Aug. 23, 2022

(54) STICKING-TYPE DEVICE FOR LIVING BODY

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 619 days.

(21) Appl. No.: 16/411,443

(22) Filed: May 14, 2019

(65) Prior Publication Data
US 2019/0350531 A1   Nov. 21, 2019

(30) Foreign Application Priority Data

May 16, 2018 (JP) .............................. JP2018-094826
Mar. 25, 2019 (JP) .............................. JP2019-056185

(51) Int. Cl.
*A61B 5/00* (2006.01)
*A61B 5/01* (2006.01)

(52) U.S. Cl.
CPC .......... *A61B 5/68335* (2017.08); *A61B 5/01* (2013.01); *A61B 5/6833* (2013.01); *A61B 5/0008* (2013.01); *A61B 2560/0214* (2013.01)

(58) Field of Classification Search
CPC ..... A61B 5/68335; A61B 5/01; A61B 5/6833; A61B 5/0008; A61B 2560/0214
USPC ........................................................ 600/549
See application file for complete search history.

(56) References Cited

U.S. PATENT DOCUMENTS

| 5,203,327 | A | * | 4/1993 | Schoendorfer | ...... | A61B 5/6833 |
| | | | | | | 600/362 |
| 5,438,984 | A | * | 8/1995 | Schoendorfer | ...... | A61B 5/4845 |
| | | | | | | 600/584 |
| 10,226,187 | B2 | * | 3/2019 | Al-Ali | ..................... | A61B 5/447 |
| 2012/0029300 | A1 | * | 2/2012 | Paquet | ................ | A61B 5/6833 |
| | | | | | | 600/300 |
| 2014/0180019 | A1 | * | 6/2014 | Martinez | ................ | A61B 5/681 |
| | | | | | | 600/300 |
| 2015/0289817 | A1 | * | 10/2015 | Augustine | .............. | A61G 7/005 |
| | | | | | | 219/217 |
| 2015/0305974 | A1 | * | 10/2015 | Ehrenreich | .......... | A61B 5/6833 |
| | | | | | | 601/46 |
| 2017/0100300 | A1 | * | 4/2017 | Rapp | .................... | A61B 5/6828 |
| 2017/0136264 | A1 | * | 5/2017 | Hyde | .................... | G16H 50/30 |

(Continued)

FOREIGN PATENT DOCUMENTS

JP   2009222543 A   10/2009

*Primary Examiner* — May A Abouelela
(74) *Attorney, Agent, or Firm* — ArentFox Schiff LLP

(57) ABSTRACT

A deep body thermometer includes an upper exterior body that is made of a foamed material of closed cells or semi-closed cells having waterproof properties and is formed in a substantially hat-like shape in side view, a lower exterior body that has a peripheral edge in close contact with the upper exterior body, a sticking member that has adhesiveness and one surface of which is stuck to an outer side surface of the lower exterior body, and a wiring substrate that is accommodated in a space defined by the upper exterior body and the lower exterior body. The upper exterior body includes stress relieving portions that extend in the direction intersecting with the direction in which stress generated by external force acts and are smoothly curved with respect to the direction in which the stress acts so as to relieve the stress.

20 Claims, 12 Drawing Sheets

(56) References Cited

U.S. PATENT DOCUMENTS

| | | | |
|---|---|---|---|
| 2019/0000341 A1* | 1/2019 | Xu | H05K 1/147 |
| 2019/0021650 A1* | 1/2019 | Lee | A61B 5/6892 |
| 2019/0029595 A1* | 1/2019 | Sekitani | A61B 5/0002 |
| 2020/0088739 A1* | 3/2020 | Rogers | B01L 3/502707 |
| 2020/0155047 A1* | 5/2020 | Rogers | B01L 3/502715 |
| 2021/0145352 A1* | 5/2021 | Rogers | A61B 5/14532 |
| 2021/0145450 A1* | 5/2021 | Gru | A61B 5/6803 |

* cited by examiner

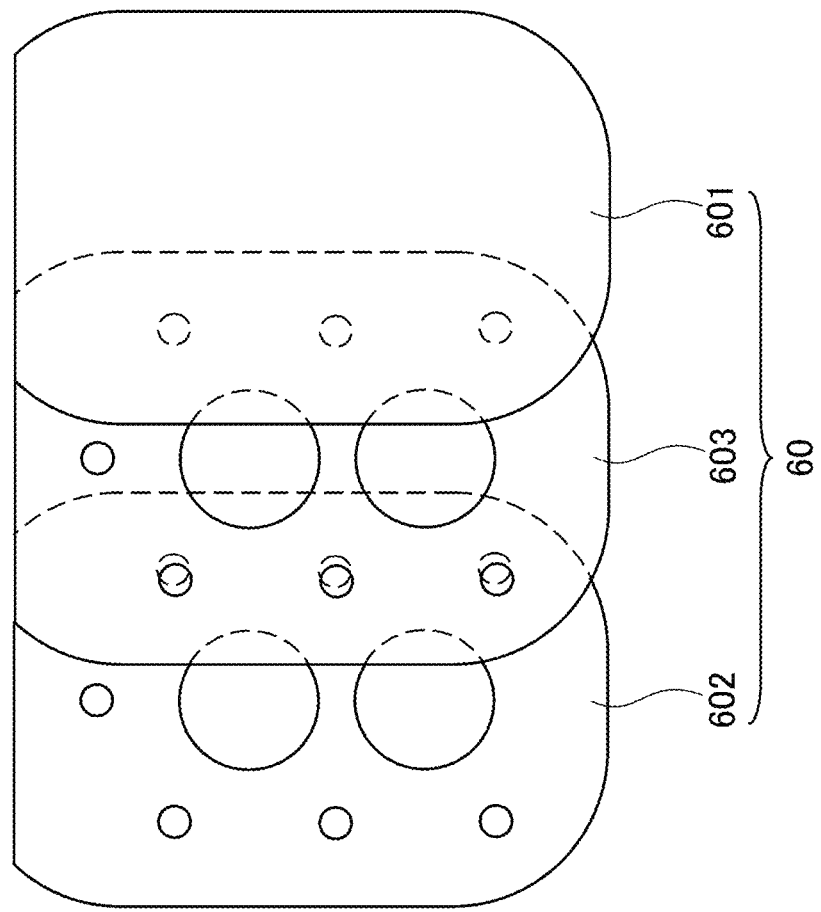
FIG. 7
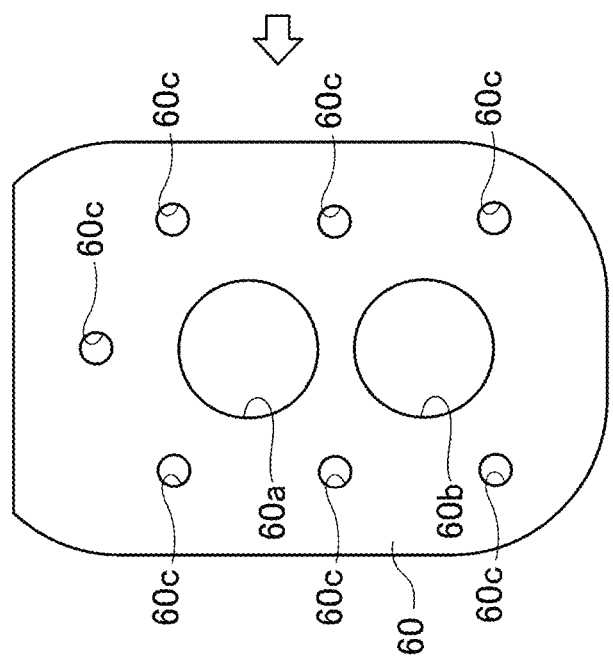

STICKING-TYPE DEVICE FOR LIVING BODY

CROSS REFERENCE TO RELATED APPLICATIONS

The present application claims priority to Japanese Patent Application No. 2018-094826, filed May 16, 2018, and Japanese Patent Application No. 2019-056185, filed Mar. 25, 2019, the entire contents of each of which are incorporated herein by reference.

FIELD OF THE INVENTION

The present invention relates to a sticking-type device for a living body that is configured to stick to the living body for use thereon.

BACKGROUND

An existing thermometer or the like has been proposed that can be stuck to a body surface to continuously measures a body temperature to acquire body temperature data. For example, Japanese Unexamined Patent Application Publication No. 2009-222543 discloses a sticking-type thermometer for continuous measurement which is stuck to a body surface of a subject and measures a deep body temperature of the subject.

More specifically, the sticking-type continuous thermometer includes a measuring unit (measuring probe) that is stuck to the body surface and measures the body temperature and a display unit that displays the deep part temperature and the like obtained based on the measured body temperature data. A main body of the measuring probe is made of a material which has constant heat capacitance and thermal conductivity and is capable of being deformed in close contact with the body surface of the living body. The shape of the main body is a substantially disc-like shape or a substantially rectangular shape, and a heat insulating material is further arranged so as to cover the main body. A first temperature detection unit is arranged at a central portion of the main body on the body surface side, and a second temperature detection unit is arranged at a position opposing the first temperature detection unit with respect to the main body. It is determined whether or not the body temperature is in a sufficiently thermally insulated state relative to an external environmental temperature based on a temperature difference between both of the temperature detection units, and the temperature of the body surface is acquired as a deep body temperature estimated value.

In the sticking-type thermometer for continuous measurement described in Japanese Unexamined Patent Application Publication No. 2009-222543, a material is used as the material of the main body, which makes close contact with the body surface, such as a foamed rubber sheet, and is easily deformed along with movement of the body with no sense of incompatibility. Foamed resin such as urethane and polystyrene is used as the heat insulating material. When a material having flexibility and plasticity is used for the main body or the heat insulating material, the sense of incompatibility at the time of sticking can be reduced but wrinkles are likely to be generated. In particular, wrinkles are likely to be generated due to the movement of the living body (body movement), a switch operation, and the like. However, in the sticking-type continuous thermometer described in Japanese Unexamined Patent Application Publication No. 2009-222543, no consideration has been given to suppressing the generation of wrinkles.

SUMMARY OF THE INVENTION

Accordingly, it is an object of the present invention to provide a sticking-type device for a living body that is configured to stick to the living body for use and is further configured for suppressing generation of wrinkles without impairing a feeling of being worn.

A sticking-type device for a living body according to an exemplary aspect includes an upper exterior body that is made of a foamed material of closed cells or semi-closed cells having waterproof properties and is formed in a substantially hat-like shape or a substantially trapezoidal shape in side view, a lower exterior body that has a peripheral edge portion making close contact with the upper exterior body, a sticking member that has adhesiveness and one surface of which is stuck to an outer side surface of the lower exterior body, and an electronic circuit that is accommodated in an accommodation space defined by the upper exterior body and the lower exterior body. Moreover, the upper exterior body includes a stress relieving portion which extends in a direction intersecting with a direction in which stress generated by external force acts and is smoothly curved with respect to the direction in which the stress acts so as to relieve the stress.

With the sticking-type device for the living body according to the exemplary aspect, the peripheral edge portion of the upper exterior body that is made of the foamed material of the closed cells or the semi-closed cells having waterproof properties and has flexibility and the peripheral edge portion of the lower exterior body are made close contact with each other, the electronic circuit is accommodated therein (in the accommodation space defined by the upper exterior body and the lower exterior body), and the sticking member is stuck to the lower exterior body. With this configuration, the sticking-type device for the living body can be stuck to the body surface of the living body in a close contact manner and cause the sticking-type device for the living body to follow movement of the living body (body movement). Therefore, a comfortable feeling of being worn can be provided. The upper exterior body includes the stress relieving portion which extends in the direction intersecting with the direction in which the stress generated by the external force acts and is smoothly curved with respect to the direction in which the stress acts so as to relieve the stress. Therefore, the stress relieving portion is deformed upon reception of the stress, so that the stress is relieved (absorbed), thereby suppressing generation of wrinkles. Further, even when the wrinkles are generated, the wrinkles are concentrated in the stress relieving portion, whereby it is possible to prevent wrinkles from being formed in other portions. As a result, it is possible to suppress the generation of wrinkles without impairing the wearing feeling.

A sticking-type device for a living body according to another exemplary aspect includes an upper exterior body that is made of a foamed material of closed cells or semi-closed cells having waterproof properties and is formed in a substantially hat-like shape or a substantially trapezoidal shape in side view, a lower exterior body that has a peripheral edge portion making close contact with the upper exterior body, a sticking member that has adhesiveness and one surface of which is stuck to an outer side surface of the lower exterior body, and an electronic circuit that is accommodated in an accommodation space defined by the upper exterior body and the lower exterior body. Moreover, the upper exterior body includes a reinforcing portion which extends substantially in parallel to a direction in which stress generated by external force acts and is formed in a substantially stripe-like shape with respect to the direction in which the stress acts so as to resist the stress.

With the sticking-type device for the living body according to the exemplary aspect, it is possible to obtain the comfortable feeling of being worn as described above. The upper exterior body includes the reinforcing portion which extends substantially in parallel to the direction in which the stress generated by the external force acts and is formed in the substantially stripe-like shape with respect to the direction in which the stress acts so as to resist the stress. Therefore, the reinforcing portion suppresses (reduces) deformation of the upper exterior body against the stress, thereby suppressing generation of wrinkles. As a result, it is possible to suppress the generation of wrinkles without impairing the wearing feeling.

Other features, elements, characteristics and advantages of the exemplary embodiments of the present invention will become more apparent from the following detailed description of preferred embodiments of the present invention (with reference to the attached drawings).

BRIEF DESCRIPTION OF THE DRAWINGS

FIG. 7 includes a plan view and an exploded view illustrating a sticking member configuring the deep body thermometer according to the first exemplary embodiment.

DETAILED DESCRIPTION OF THE EXEMPLARY EMBODIMENTS

Figure 1:
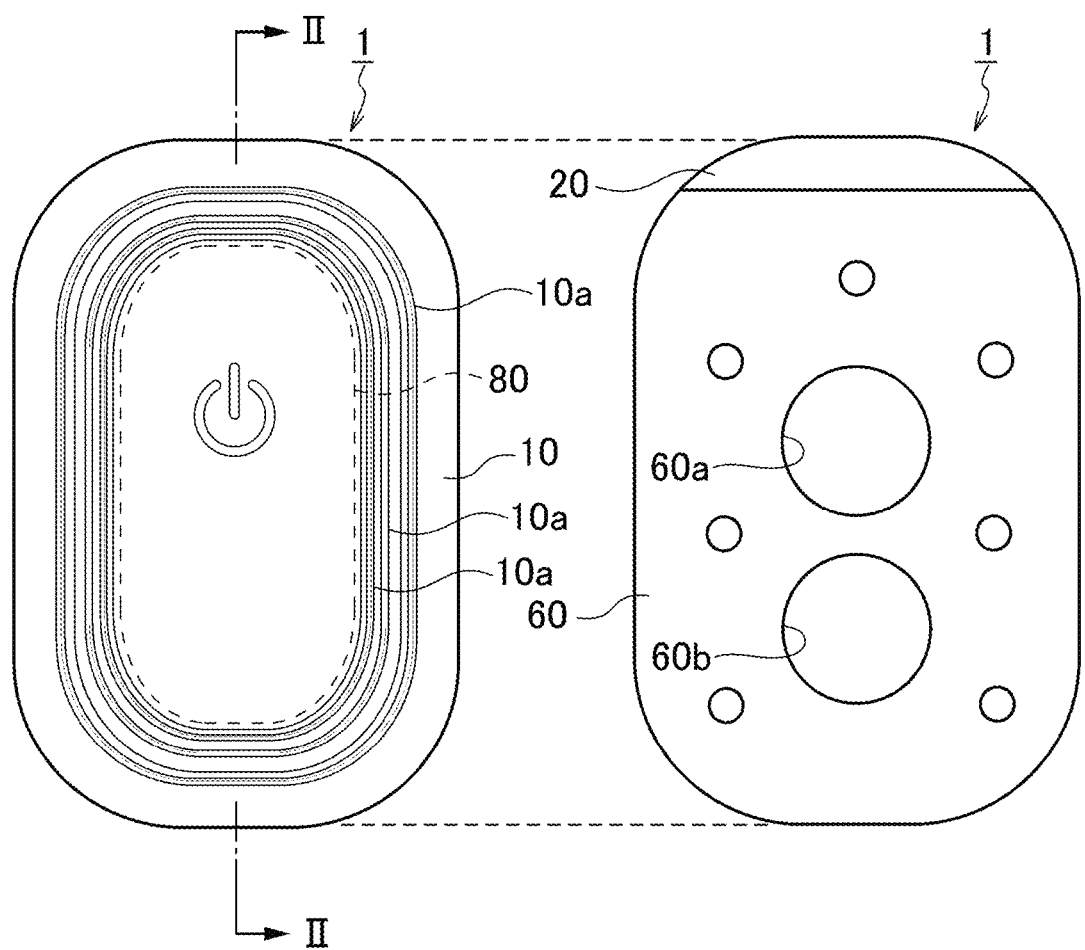
FIG. 1 includes a plan view and a bottom view illustrating an appearance of a deep body thermometer according to a first exemplary embodiment.

Hereinafter, exemplary embodiments of the invention will be described in detail with reference to the accompanying drawings. In the drawings, the same reference numerals are used to designate the same or corresponding parts. In the drawings, the same elements are denoted by the same reference numerals, and description thereof will not be repeated. Here, a non-heating-type deep body thermometer (hereinafter simply referred to as a "deep body thermometer") will be described as an example of a sticking-type device for a living body according to the invention.

First Exemplary Embodiment

Figure 2:
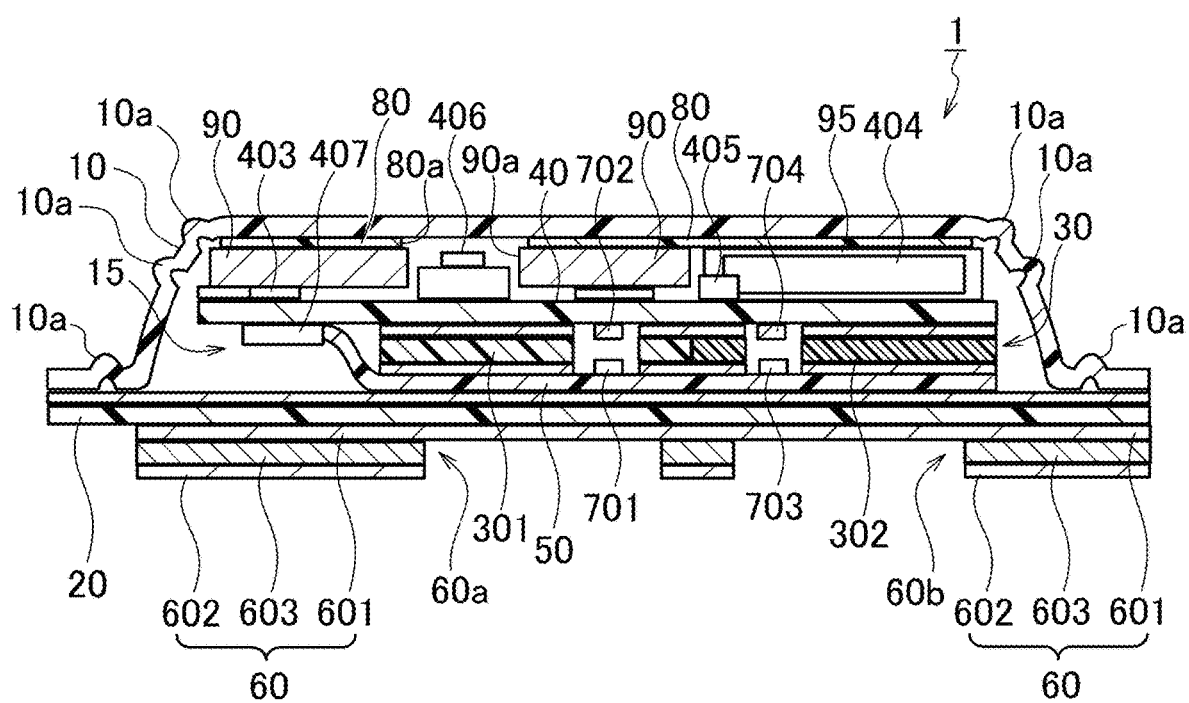
FIG. 2 is a cross-sectional view illustrating the configuration of the deep body thermometer according to the first exemplary embodiment.
Figure 3:
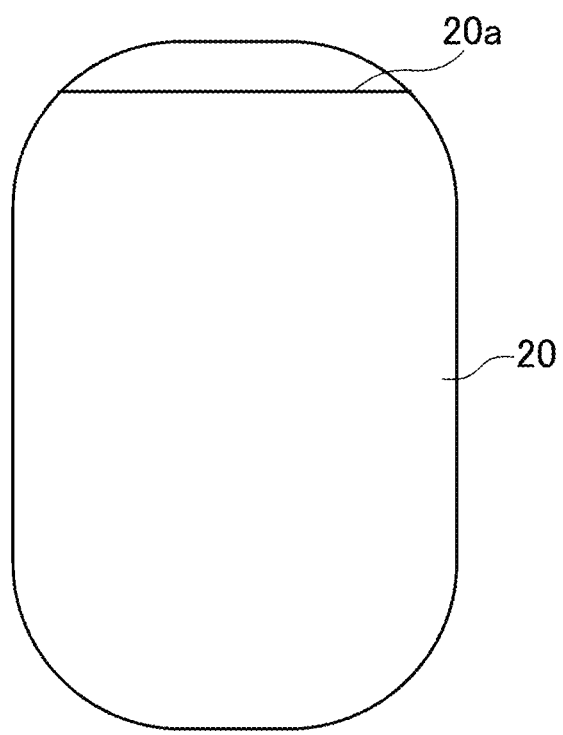
FIG. 3 is a plan view illustrating a lower exterior body configuring the deep body thermometer according to the first exemplary embodiment.
Figure 4:
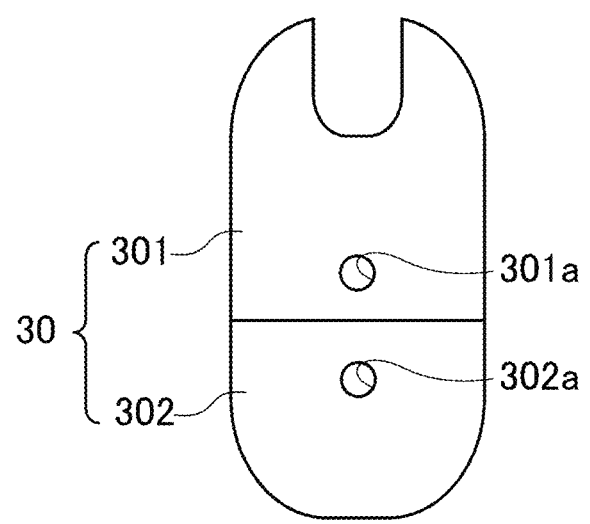
FIG. 4 is a plan view illustrating a thermal resistor layer configuring the deep body thermometer according to the first exemplary embodiment.
Figure 5:
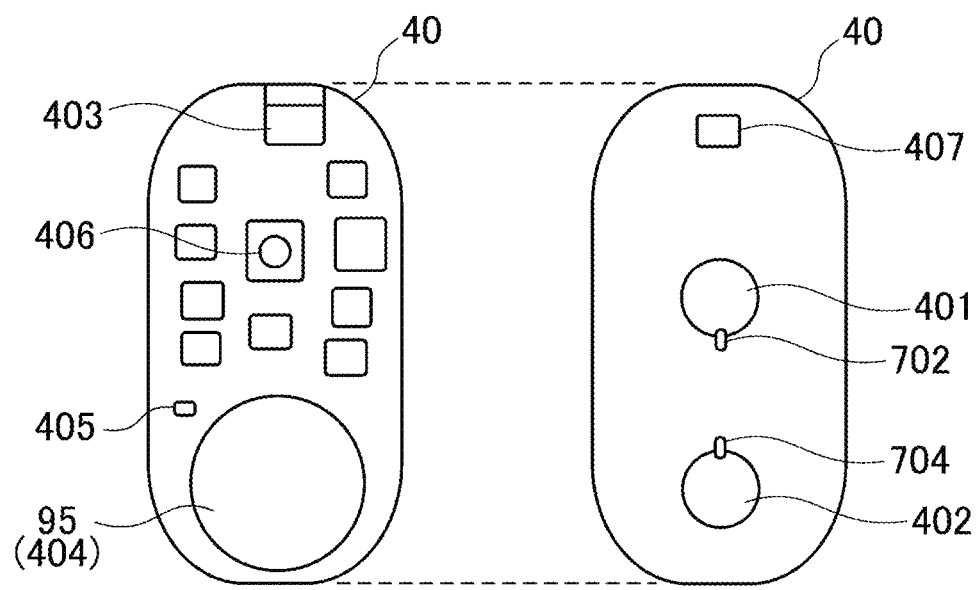
FIG. 5 includes a plan view and a bottom view illustrating a wiring substrate configuring the deep body thermometer according to the first exemplary embodiment.
Figure 6:
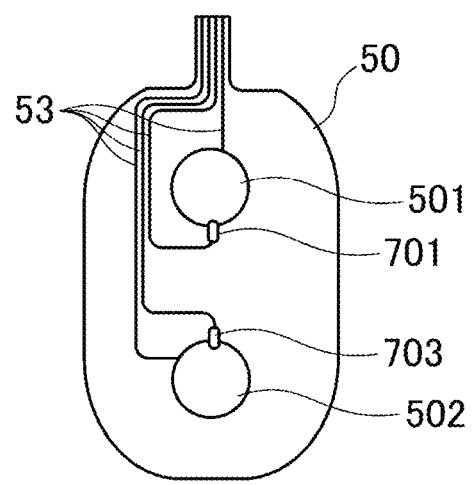
FIG. 6 is a plan view illustrating a flexible substrate configuring the deep body thermometer according to the first exemplary embodiment.

First, the configuration of a deep body thermometer 1 according to a first exemplary embodiment will be described with reference to FIG. 1 to FIG. 7. FIG. 1 includes a plan view and a bottom view illustrating an appearance of the deep body thermometer 1. FIG. 2 is a cross-sectional view (cross-sectional view taken along a line II-II in FIG. 1) illustrating the configuration of the deep body thermometer 1. FIG. 3 is a plan view illustrating a lower exterior body 20 configuring the deep body thermometer 1. FIG. 4 is a plan view illustrating a thermal resistor layer 30 configuring the deep body thermometer 1. FIG. 5 includes a plan view and a bottom view illustrating a wiring substrate 40 configuring the deep body thermometer 1. FIG. 6 is a plan view illustrating a flexible substrate 50 configuring the deep body thermometer 1. FIG. 7 includes a plan view and an exploded view illustrating a sticking member 60 configuring the deep body thermometer 1.

The deep body thermometer 1 is a non-heating-type deep body thermometer that is configured to obtain a heat flow rate from a deep body of a user (subject) based on a difference between temperatures corresponding to biological signals detected by a first temperature sensor 701 and a second temperature sensor 702 and a difference between temperatures corresponding to biological signals detected by a third temperature sensor 703 and a fourth temperature sensor 704 and thus configured to acquire a deep body temperature. The deep body thermometer 1 is a sticking-type (patch-type) deep body thermometer that is configured to be stuck (or adhere) to the body surface of the user (subject) and to continuously measure the body temperature to acquire body temperature data. In particular, the deep body thermometer 1 is configured to suppress generation of wrinkles without impairing the comfortable feeling of being worn.

According to an exemplary aspect, the deep body thermometer 1 includes an upper exterior body 10, the lower exterior body 20, a body temperature measuring unit 15, a lining member 80, a buffer member 90 and the sticking member 60. The body temperature measuring unit 15 mainly includes the thermal resistor layer 30, the wiring substrate 40 in or on which the second temperature sensor 702 and the fourth temperature sensor 704 are mounted, and the flexible substrate 50 in or on which the first temperature sensor 701 and the third temperature sensor 703 are mounted.

Hereinafter, the components will be described in detail. The upper exterior body 10 is made of, for example, a foamed material of closed cells or semi-closed cells having flexibility, waterproof properties, and heat retaining properties. In order to prevent the temperature of the body temperature measuring unit 15 from being locally changed due to a sudden variation (change) in an outside air temperature, it is preferable to use a foamed material having low thermal conductivity for the upper exterior body 10. As the material, for example, polyurethane, polystyrene, polyolefin, or the like is preferably used. The upper exterior body 10 is formed in a substantially hat-like shape in cross section such that the body temperature measuring unit 15 (the thermal resistor layer 30, the wiring substrate 40, the flexible substrate 50, and the like) can be accommodated therein. That is, the upper exterior body 10 includes a substantially rectangular top surface portion having rounded corners, a substantially annular bottom portion concentrically formed in an outer side portion of the top surface portion in plan view, and a coupling portion coupling the top surface portion and the bottom portion. Therefore, the side surface of the thermal resistor layer 30 is covered with the foamed material, and the side surface of the thermal resistor layer 30 is prevented from being exposed to the outside air.

Stress relieving portions 10a (corresponding to a projecting member or a recess as described herein) that are smoothly curved with respect to the direction in which stress generated by external force applied from the outside acts are formed on the surface of the upper exterior body 10 so as to relieve (absorb) the stress. The stress relieving portions 10a are formed, for example, in such shapes (corresponding to the recess portion) that the longitudinal cross sections thereof are recessed in substantially semicircular forms or in such shapes (corresponding to the projecting portion) that they project in substantially semicircular forms. In an exemplary aspect, the stress relieving portions 10a can be formed to have the longitudinal cross sections of substantially wavy shapes or substantially bellows-like shapes. The direction in which the stress acts can be specified by, for example, structure analysis (simulation), an experiment using a strain gauge, or the like.

The stress relieving portions 10a are formed so as to extend in the direction intersecting with the direction in which the stress acts (for example, in a vertical or substantially vertical direction thereto). More specifically, the stress relieving portions 10a are provided concentrically with the outer edge (outline) of the top surface (top surface portion) of the upper exterior body 10 along the outer edge of the top surface (that is, in the circumferential direction) in plan view. In particular, the stress relieving portions 10a are provided concentrically with the outer edge of the lining member 80 in an outer side portion of an outer edge position of the lining member 80 in plan view. In the exemplary embodiment, as illustrated in FIG. 1, three stress relieving portions 10a are arranged concentrically with the outer edge of the lining member 80. It should be noted that the stress relieving portions 10a are not necessarily have to be connected in substantially annular shapes and may be partly cut off.

As a method of processing the upper exterior body 10, for example, vacuum molding is preferably used. That is, after a sheet made of a foamed material is placed on a mold, the sheet is heated by a heater, and vacuum suction is carried out from the mold side, whereby the softened sheet is stuck to the mold. Thus, the upper exterior body 10 is formed. In this case, the stress relieving portions 10a or reinforcing portions (reinforcing ribs) 10b, which will be described later, are formed simultaneously. In the case where the upper exterior body 10 is formed by the vacuum molding, since a side surface portion thereof is extended (i.e., the deformation amount thereof is increased), the thickness of the side surface portion tends to be reduced.

The lower exterior body 20 is formed of, for example, a non-foamed resin film having waterproof properties (low moisture permeability) and higher thermal conductivity than that of the upper exterior body 10. Examples of the material include polypropylene, polyethylene, polyester, polyimide, and the like, and polyethylene terephthalate (PET) is particularly preferably used. The lower exterior body 20 is formed in a substantially flat plate shape (flat) such that the flexible substrate 50 (body temperature measuring unit 15) to which the first temperature sensor 701 and the third temperature sensor 703 are attached can be fixed thereto in a close contact manner. The body temperature measuring unit 15 and the lower exterior unit 20 are preferable fixed in the close contact manner by bonding with a double-sided adhesive tape, fixing with an adhesive, or the like because a gap between the body temperature measuring unit 15 and the lower exterior unit 20 causes thermal resistance to vary and this influences heat fluxes. The upper exterior body 10 and the lower exterior body 20 are formed to have the same (or substantially the same) sizes (outer dimensions) and are formed to have sizes of, for example, about 40 to 100 mm in the longitudinal direction and about 20 to 60 mm in the lateral direction.

A peripheral edge portion of the upper exterior body 10 having the substantially hat-shaped cross section and a peripheral edge portion of the lower exterior body 20 formed in the substantially flat plate shape are fixed in a close contact manner by, for example, bonding with a double-sided adhesive tape, fixing with an adhesive, heat sealing, or the like. In order to be waterproof, it is desirable that a portion where the upper exterior body 10 and the lower exterior body 20 are fixed in the close contact manner is substantially flat and has a structure in which wrinkles are less likely to be formed. That is, it is preferable that the outer edge portion of the lower exterior body 20 be substantially flat, the outer edge portion of the opposing upper outer member 10 be also substantially flat, and they be stuck and fixed to each other in the close contact manner. In this case, since force is uniformly applied to the portion where the upper exterior body 10 and the lower exterior body 20 are fixed in the close contact manner, the problem, such as generation of wrinkles, that the waterproof performance is adversely affected hardly occurs.

As illustrated in FIG. 2, the body temperature measuring unit 15 is formed by laminating the flexible substrate 50, the thermal resistor layer 30, and the wiring substrate 40 in this order from the lower exterior body 20 side.

According got the exemplary aspect, the thermal resistor layer 30 includes two thermal resistors having different thermal resistance values, i.e., a first thermal resistor 301 and a second thermal resistor 302 to form two heat fluxes (see FIG. 4). As the first thermal resistor 301, a material having higher thermal conductivity (a lower heat resistance value) than that of the second thermal resistor 302, for example, plastics such as polypropylene, polyethylene, acrylic, polycarbonate, and epoxy resin is preferably used. As the second thermal resistor 302, a material having lower thermal conductivity (a higher thermal resistance value) than that of the first thermal resistor 301, for example, foamed plastic (foamed material) such as polyurethane, polystyrene, and polyolefin is preferably used. However, plastic, rubber, or the like which is not foamed may also be used. The thermal conductivity of metal such as copper and aluminum is equal to or higher than about 100 [W/m/K] whereas the thermal conductivity of plastics such as polypropylene, polyethylene, acrylic, polycarbonate, and epoxy resin is about 0.1 to 0.5 [W/m/K] and is lower by about three digits. The thermal conductivity of the foamed plastic is much lower than that by almost one digit. The thermal conductivity of the air is much lower and is about 0.024 [W/m/K]. The first thermal resistor 301 and the second thermal resistor 302 are formed to have substantially the same thickness in order to reduce cost by enabling the wiring substrate 40 and the flexible substrate 50 to be laminated on each other.

As further shown in FIG. 4, a first through-hole 301a penetrating in the thickness direction is formed in the first thermal resistor 301 configuring the thermal resistor layer 30. Similarly, a second through-hole 302a penetrating in the thickness direction is formed in the second thermal resistor 302 configuring the thermal resistor layer 30. The first through-hole 301a is formed such that the first temperature sensor 701 and the second temperature sensor 702 are housed in an inner side portion thereof in plan view. In other words, the first temperature sensor 701 and the second temperature sensor 702 which are paired are arranged inside (in the inner side portion of) the first through-hole 301a along the thickness direction of the first thermal resistor 301. Similarly, the second through-hole 302a is formed such that the third temperature sensor 703 and the fourth temperature sensor 704 are housed in an inner side portion thereof in plan view. In other words, the third temperature sensor 703 and the fourth temperature sensor 704 which are paired are arranged inside (in the inner side portion of) the second through-hole 302a along the thickness direction of the second thermal resistor 302.

According to the exemplary aspect, the first temperature sensor 701 to the fourth temperature sensor 704 (hereinafter, also collectively referred to as "temperature sensors (corresponding to a biological sensor described in the disclosure) 70"), for example, thermistors, temperature measuring resistors, or the like whose resistance values vary depending on temperatures are preferably used. It is preferable that the temperature sensors 70 have small heat capacitance as much as possible from the viewpoint of enhancing responsiveness. Therefore, for example, chip thermistors are preferably used as the temperature sensors 70. Each of the first temperature sensor 701 to the fourth temperature sensor 704 is electrically connected to a processing circuit, which will be described later, with a printed wiring interposed therebetween, and electric signals (i.e., voltage values) corresponding to the temperatures are read by the processing circuit.

In order to reduce the size of the thermal flow-type deep body thermometer 1, it is important to make the thermal resistor layer 30 (the first thermal resistor 301 and the second thermal resistor 302) small. However, when the thermal resistor layer 30 (the first thermal resistor 301 and the second thermal resistor 302) is made small, differences in an output value between the paired temperature sensors 70 become small and measurement errors can therefore be increased. Since the temperature sensors 70 (chip thermistors) have substantially rectangular parallelepiped shapes and have some thickness, the thickness of the temperature sensors 70 cannot be ignored when the thickness of the thermal resistor layer 30 (the first thermal resistor 301 and the second thermal resistor 302) is made thinner. When the temperature sensors 70 (chip thermistors) are in contact with the side surface of the thermal resistor layer 30 (the first thermal resistor 301 and the second thermal resistor 302), heat is transferred thereto from the contact portions. Due to this, the temperatures (detected values) of the temperature sensors 70 (chip thermistors) may become temperatures (values) deviating from the surface temperature of the thermal resistor layer 30 (the first thermal resistor 301 and the second thermal resistor 302). In order to cope with this (to reduce the influences thereby), the through-holes 301a and 302a are formed in the thermal resistor layer 30 (the first thermal resistor 301 and the second thermal resistor 302) around the temperature sensors 70 (chip thermistors) such that the temperature sensors 70 (chip thermistors) do not make contact with the side surface of the thermal resistor layer 30 (the first thermal resistor 301 and the second thermal resistor 302).

The wiring substrate 40 (corresponding to an electronic circuit as described herein) is a rigid substrate such as a glass epoxy substrate, for example. In or on the wiring substrate 40, there is mounted the processing circuit that processes the output signals from the first temperature sensor 701 to the fourth temperature sensor 704 and acquires deep body temperature data. In addition, a wireless communication unit 403 that transmits (outputs) the acquired deep body temperature data and a coin battery 404 that supplies power to the processing circuit and the wireless communication unit 403 are mounted in or on the wiring substrate 40. The processing circuit mainly includes a temperature input circuit and an arithmetic processing circuit. The temperature input circuit is configured to include, for example, an amplifier (for example, an operational amplifier), an analog/digital converter (an A/D converter), and the like for reading the detection signals (output voltages) of the temperature sensors 70. The temperature input circuit amplifies the analog signals output from the temperature sensors 70, converts the analog signals into digital signals, and outputs the digital signals to the arithmetic processing circuit.

The arithmetic processing circuit calculates the deep body temperature from the read measurement (temperature) data. The arithmetic processing circuit includes, for example, an MCU (Micro Control Unit), an EEPROM, a RAM, and the like, and calculates the deep body temperature based on the detected values of the temperature sensors 70, which have been read by the temperature input circuit. The arithmetic processing circuit stores the calculated deep body temperature data in a memory such as the RAM. Further, the arithmetic processing circuit outputs the calculated deep body temperature data to the wireless communication unit 403 to output (transmit) the calculated deep body temperature data to an external device wirelessly.

The arithmetic processing circuit is configured to calculate (i.e., estimate) the deep body temperature based on the temperature difference between the front and back surfaces of the thermal resistors 301 and 302, which is caused by the difference between the two heat fluxes formed using the two thermal resistors 301 and 302 having different thermal resistances. More specifically, the arithmetic processing circuit calculates the deep body temperature Tb based on the following equation (1), for example.

$$Tb=\{T1(T3-T4)*Ra1-T3(T1-T2)*Ra2\}/\{(T3-T4)*Ra1-(T1-T2)*Ra2\} \quad (1)$$

Here, Tb represents a deep body temperature, T1 represents a temperature detected by the first temperature sensor 701, T2 represents a temperature detected by the second temperature sensor 702, and Ra1 represents a thermal resistance value of the first thermal resistor 301. In addition, T3 represents a temperature detected by the third temperature sensor 703, T4 represents a temperature detected by the fourth temperature sensor 704, and Ra2 represents a thermal resistance value of the second heat resistor 302.

Since Ra1 and Ra2 are known, the deep body temperature Tb can be uniquely determined by detecting the four temperatures (T1, T2, T3, T4).

On the lower surface of the wiring substrate 40, the second temperature sensor 702 that acquires the temperature of the upper surface (outside air side) of the first thermal resistor 301 and the fourth temperature sensor 704 that detects the temperature of the upper surface (outside air side) of the second thermal resistor 302 are mounted. More specifically, thermal equalization patterns 401 and 402 for equalizing peripheral temperature distribution are formed on the lower surface of the wiring substrate 40, one electrode of the second temperature sensor 702 is connected to the thermal equalization pattern 401, and one electrode of the fourth temperature sensor 704 is connected to the thermal equalization pattern 402. The thermal equalization patterns 401 and 402 are made of, for example, a material having high thermal conductivity, such as a metal film.

In order to prevent the temperature of only a part of the wiring substrate 40 from being changed due to influences of the outside air temperature and the like, it is preferable to provide, on the back surface side (outside air side) of the wiring layer on which the second temperature sensor 702 and the fourth temperature sensor 704 are mounted, an equalization member (metal film) having high thermal conductivity configured to thermally equalize the influences of the temperature distribution of the outside air temperature. As the equalization member, a metal foil, a metal thin plate, or the like may be used, but it is desirable to form it as a wiring pattern (solid pattern) of the inner layer of the wiring substrate 40 (multilayer rigid substrate) similarly to the wiring layer formed on the wiring substrate 40. In this case, the wiring pattern (solid pattern) of the inner layer, which is used as the equalization member, may be a ground pattern but is preferably an independent pattern which is connected to no electric circuit and through which no current flows.

The wireless communication unit 403 transmits the acquired deep body temperature data (biological information) to an external management device or an information terminal (for example, a smart phone or the like). The wireless communication unit 403 transmits the deep body temperature data to the external management device or the information terminal using, for example, Bluetooth (registered trademark) or the like. The thin coin battery 404 supplies electric power to the processing circuit (electronic component), the wireless communication unit 403, and the like described above. The coin battery 404 is accommodated in a battery holder 95 mounted in or on (attached to) the wiring substrate 40. The battery holder 95 is disposed between the wiring substrate 40 and the lining member 80. That is, the battery holder 95 also serves as a spacer member supporting the lining member 80. In order to reduce a flat area (sticking area) of the body temperature measuring unit 15 (deep body thermometer 1) and to prevent influences of heat generation caused by change in the outside air temperature and operations of the wireless communication unit 403, the wireless communication unit 403 and the coin battery 404 (battery holder 95) are disposed on the opposite side (upper surface side) to the temperature sensors 70 with the wiring substrate 40 interposed therebetween.

A power supply switch 406 (corresponding to an operation switch as described herein) that receives an ON/OFF operation of a power supply by the user with the upper exterior body 10 interposed therebetween is mounted on the upper surface (main surface) of the wiring substrate 40. The wiring substrate 40 is accommodated in a sealed space defined by the upper exterior body 10 and the lower exterior body 20 such that the power supply switch 406 opposes the back surface (rear surface) of the upper exterior body 10. As the power supply switch 406, for example, a push button switch, a rocker switch, or the like is preferably used. In the case of the push button switch, a push button switch employing an alternate operation of holding an ON state even when a fingertip is separated therefrom is preferably used. The power supply switch 406 is preferably a surface mount type, but a lead type may also be used.

In order to prevent the power supply switch 406 from being erroneously (accidentally) pressed to turn ON/OFF the power supply and prevent the power supply switch 406 from pushing up the upper exterior body 10, the power supply switch 406 is disposed so as not to make contact with the upper exterior body 10. To be more specific, a gap between a button upper surface (top surface) of the power supply switch 406 and the back surface (rear surface) of the upper exterior body 10 is preferably set to a range of about 0 to 4 mm, and more preferably set to a range of about 0.5 to 1.5 mm, for example. The stroke of the power supply switch 406 is preferably set to a range of about 0.1 to 1 mm, and more preferably set to a range of about 0.1 to 0.3 mm, for example.

On the upper surface of the wiring substrate 40, an LED (Light Emitting Diode) 405 which lights or flickers in accordance with a user's operation and a body temperature measurement state (for example, ON/OFF of the power supply switch 406, start/end of measurement, and the like) is mounted. Instead of the LED, for example, a VCSEL or the like may be used. An FPC connector 407 for electrically connecting the flexible substrate 50 is attached to the lower surface side of the wiring substrate 40.

The flexible substrate (FPC) 50 is made of, for example, polyimide, polyester (PET), or the like and has flexibility. In or on the flexible substrate 50, the first temperature sensor 701 that acquires the temperature of the first thermal resistor 301 on the skin side and the third temperature sensor 703 that acquires the temperature of the second thermal resistor 302 on the skin side are mounted. More specifically, as illustrated in FIG. 6, in order to equalize the peripheral temperature distribution, thermal equalization patterns 501 and 502 are formed on the flexible substrate 50. One terminal of the first temperature sensor 701 is connected to the thermal equalization pattern 501, and one terminal of the third temperature sensor 703 is connected to the thermal equalization pattern 502. The thermal equalization patterns 501 and 502 are made of, for example, a material having high thermal conductivity, such as a metal film. Each of the first temperature sensor 701 and the third temperature sensor 703 is connected to the wiring substrate 40 (processing circuit) with wiring patterns 53 and the FPC connector 407 interposed therebetween, and electric signals (voltage values) corresponding to the temperatures are read by the processing circuit (temperature input circuit). As described above, the lower exterior body 20, the flexible substrate 50, the thermal resistor layer 30 and the wiring substrate 40 are fixed to each other in a close contact manner by, for example, a double-sided adhesive tape or the like so as to form no gap therebetween in order to form the heat fluxes.

The lining member 80 formed in a substantially thin plate shape (sheet shape) thinner than the buffer member 90, which will be described later, is disposed on the back surface (rear surface) of the upper exterior body 10, that is, between the upper exterior body 10 and the buffer member 90 and the battery holder (spacer member) 95. The lining member 80 is formed to have a substantially similar shape to the outer edge of the top surface of the upper exterior body 10 in plan view. The lining member 80 is arranged concentrically with the outer edge of the top surface of the upper exterior body 10. In order to suppress wrinkles on the upper exterior body 10, one surface of the lining member 80 is stuck to and attached to the back surface (rear surface) of the upper exterior body 10 by, for example, a double-sided adhesive tape or the like. The lining member 80 is made of, for example, a resin material such as PET having flexibility so as to have deflection properties (be capable of being curved) in the operating direction (for example, in the press-down direction) of the power supply switch 406. The lining member 80 may be made of a thin metal plate or the like.

In the lining member 80, a through-hole 80a in which the power supply switch 406 is housed in an inner side portion in plan view is formed in the thickness direction. The circumference of the through-hole 80a may be completely closed or may not be completely closed. The through-hole 80a of the lining member 80 is formed to have such size that it is smaller than the outer diameter of the fingertip so as not to cause the whole fingertip to enter the through-hole 80a and the belly of the fingertip is inserted into it so as to press the power supply switch 406. More specifically, since the outer diameter of the fingertip differs from person to person, the inner diameter of the through-hole 80a is preferably set to a range of about 10 to 20 mm, for example, and more preferably set to a range of about 13 to 16 mm. When the upper exterior body 10 is thick (for example, equal to or more than about 2 mm), the inner diameter of the through-hole 80a is preferably made larger in accordance with the thickness of the upper exterior body 10.

Between the upper surface (main surface) of the wiring substrate 40 and the lining member 80, the buffer member 90 which has buffer properties (cushioning properties) and is formed in a substantially plate shape is disposed. The buffer member 90 is formed to be thicker than the height (height length) of the power supply switch 406 mounted in or on the wiring substrate 40 from the mounting surface of the wiring substrate 40 and the height (height length) of the electronic component from the mounting surface of the wiring substrate 40. The buffer member 90 is stuck and attached to the other surface of the lining member 80 by, for example, a double-sided adhesive tape or the like.

In the buffer member 90, a through-hole 90a in which the power supply switch 406 is housed in an inner side portion in plan view is formed in the thickness direction. The through-hole (cavity) 90a formed in the buffer member 90 is formed and disposed so as to be housed in the inner side portion of the through-hole (cavity) 80a formed in the lining member 80 in plan view. That is, the through-hole 90a of the buffer member 90 is formed to be smaller than the through-hole 80a of the lining member 80. The through-hole 90a formed in the buffer member 90 and the through-hole 80a formed in the lining member 80 are formed in substantially circular shapes (including substantially oval shapes, for example), and the inner diameters thereof are set (formed) to be smaller than the outer diameter of the fingertip. More specifically, the inner diameter of the through-hole 90a of the buffer member 90 is preferably set to a range of, for example, about 8 to 18 mm, and more preferably set to a range of about 11 to 14 mm. When the upper exterior body 10 is thick (for example, equal to or larger than about 2 mm), the inner diameter of the through-hole 90a is preferably made larger in accordance with the thickness thereof.

As illustrated in FIG. 7, the sticking member 60 includes a first adhesive layer 601 which is stuck to the outer surface of the lower exterior body 20, a ventilation layer 603 (i.e., a moisture permeable layer transmitting moisture) which is stuck to the first adhesive layer 601 and has ventilation properties, and a second adhesive layer 602 which is stuck to the ventilation layer 603. When the deep body thermometer 1 is stuck to the skin for use, sweat accumulated between the skin and the deep body thermometer 1 (lower exterior body 20) for a long time may cause the skin to be inflamed. By providing the ventilation layer 603 which is moisture penetrating in the sticking member 60, stuffiness by sweat or the like is suppressed. As the ventilation layer 603 (moisture permeable layer), for example, a nonwoven fabric can be suitably used. In place of the nonwoven fabric, cloth or knitted fabric may be used. Further, paper, wood, sponge/foamed material of open-cells, or the like may be used, or a plastic, rubber, or metal structure having grooves or holes extending from the center of the body temperature measuring unit 15 toward the peripheral edge thereof may be used.

Since the ventilation layer 603 (moisture permeable layer) contains the air therein, the heat conductivity thereof is usually low. Therefore, when the ventilation layer 603 (moisture permeable layer) is provided between the sensors and the like and the skin, the body temperature measurement accuracy is affected. In consideration of this (in order to stably measure the body temperature), the ventilation layer 603 (moisture permeable layer) is not arranged in a region overlapping with the first temperature sensor 701 and the third temperature sensor 703 which measure the temperatures of the skin and the thermal equalization patterns 501 and 502 connected to them.

Here, the case where the nonwoven fabric is used as the ventilation layer 603 (moisture permeable layer) will be described as an example. As illustrated in FIG. 7, double-sided adhesive tapes (the first adhesive layer 601 and the second adhesive layer 602) having biocompatibility are stuck to both sides of the nonwoven fabric (the ventilation layer 603). In the ventilation layer 603 and the second adhesive layer 602, through-holes 60a and 60b in which the first temperature sensor 701 and the third temperature sensor 703 are housed in inner side portions in plan view are formed in the thickness direction. It is preferable that no through-hole be formed in the double-sided adhesive tape (first adhesive layer 601) to be stuck to the lower exterior body 20. This is because when the through-hole is formed therein (i.e., when the first adhesive layer 601 is not present), the lower exterior body 20 does not make close contact with the skin and the measurement accuracy may be lowered.

In general, since the double-sided adhesive tape (second adhesive layer 602) is inferior in the moisture permeability to the nonwoven fabric (ventilation layer 603), it is preferable to form a plurality (seven in the example illustrated in FIG. 7) of through-holes 60c formed in the thickness direction in at least the second adhesive layer 602. In this case, for example, it is preferable to arrange the through-holes 60c having the diameter of about 1 to 10 mm with intervals of about 2 to 20 mm. Instead of the through-holes 60c, for example, a notch having a crossing portion (i.e., a notch intersecting in a substantially cross shape) may be formed. In this case, it is preferable to arrange the intersecting notches having the length of about 1 to 10 mm with intervals of about 2 to 20 mm.

Figure 8:
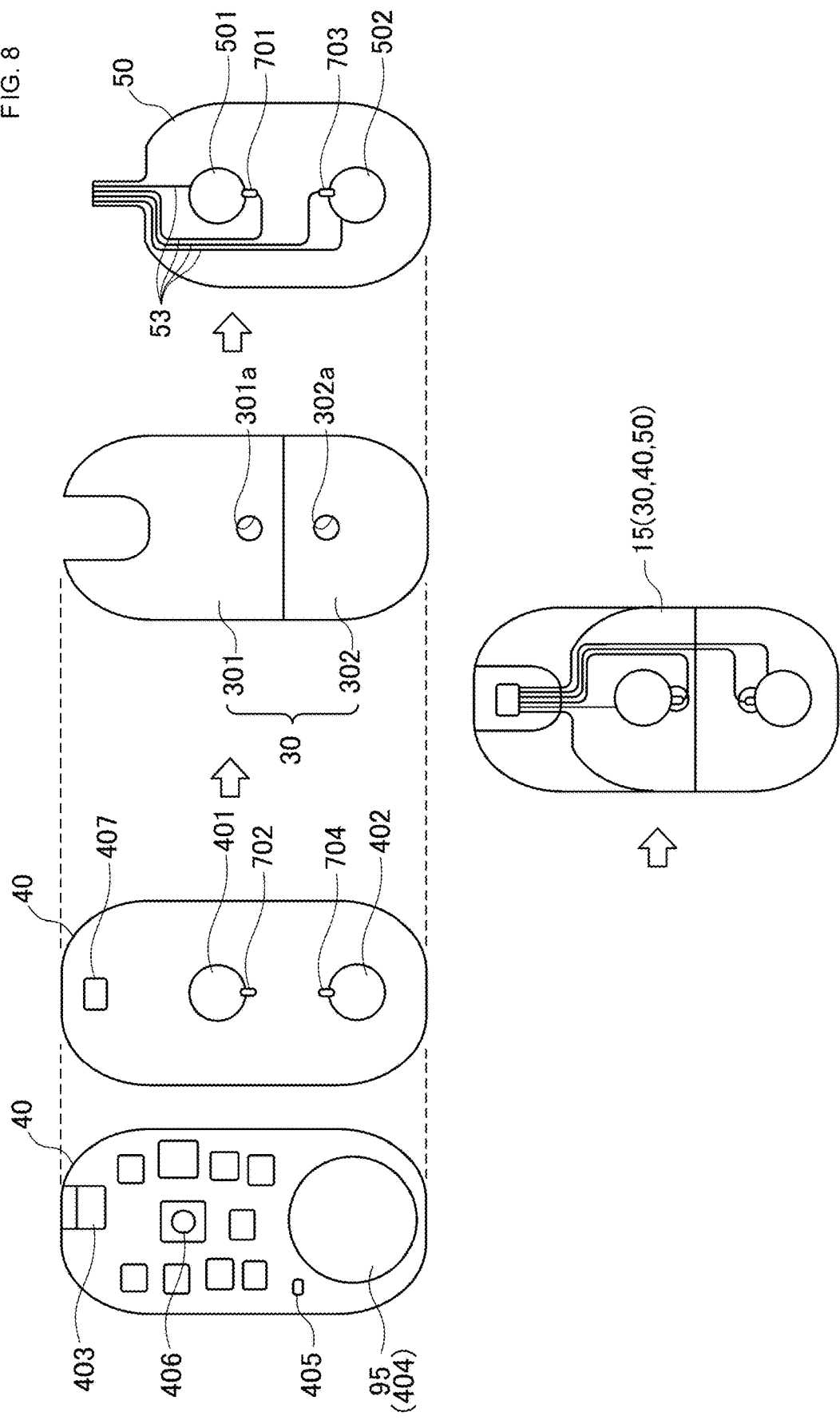
FIG. 8 is a view (part 1) for explaining a method of assembling the deep body thermometer according to the first exemplary embodiment.
Figure 9:
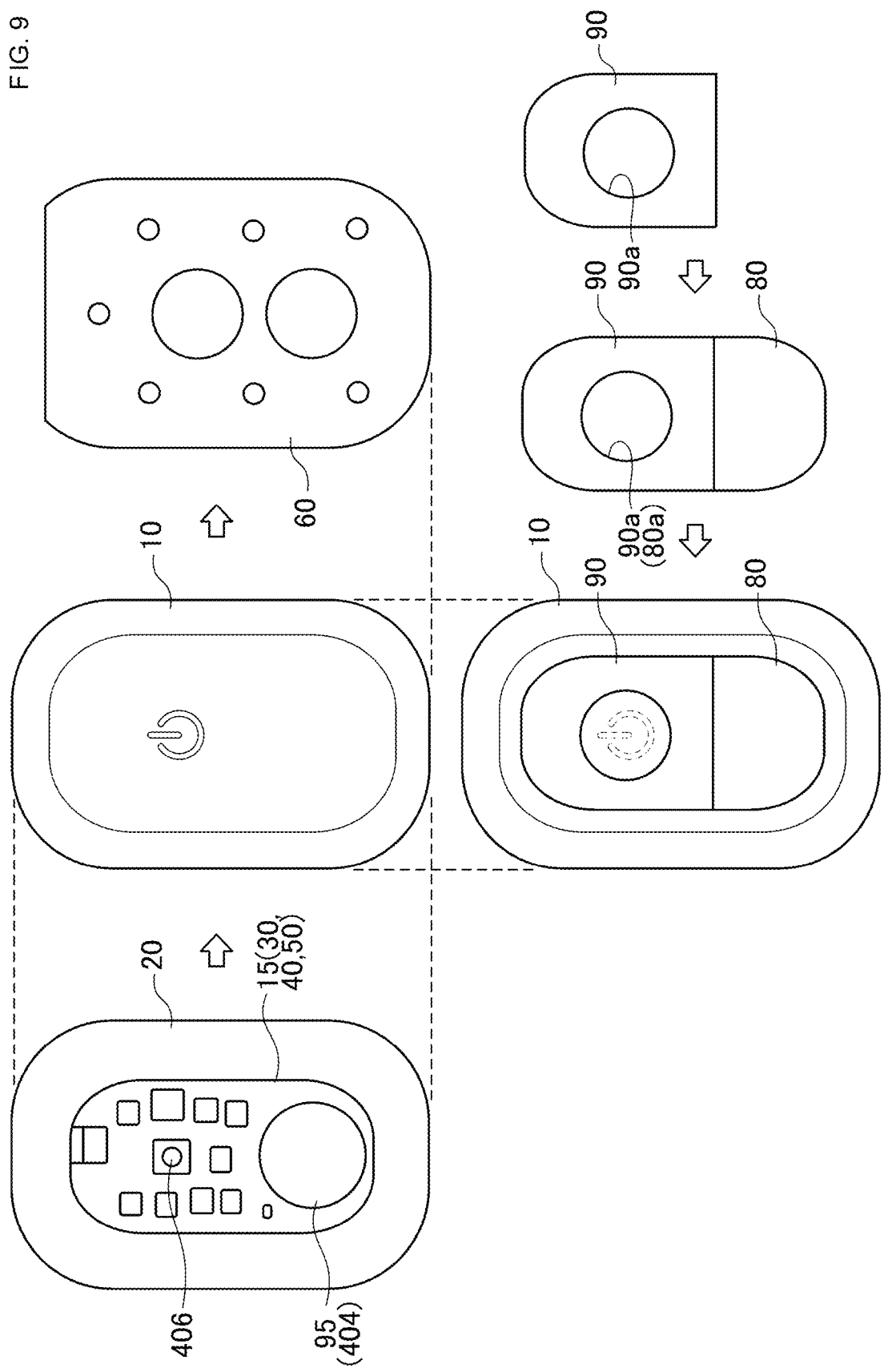
FIG. 9 is a view (part 2) for explaining the method of assembling the deep body thermometer according to the first exemplary embodiment.

Next, a method of assembling the deep body thermometer 1 (i.e., manufacturing method) will be described with reference to FIGS. 8 and 9. FIG. 8 is a view (part 1) for explaining the method of assembling the deep body thermometer 1. FIG. 9 is a view (part 2) for explaining the method of assembling the deep body thermometer 1.

The deep body thermometer 1 is assembled in the following steps (1) to (6), for example.

Step (1) One surface of the thermal resistor layer 30 (the first thermal resistor 301 and the second thermal resistor 302) is fixed to the back surface of the wiring substrate 40 in a close contact manner by a double-sided adhesive tape.

Step (2) After the flexible substrate 50 is connected to the FPC connector 407 of the wiring substrate 40, the flexible substrate 50 is fixed to the other surface of the thermal resistor layer 30 (the first thermal resistor 301 and the second thermal resistor 302) in a close contact manner by a double-sided adhesive tape.

Step (3) The coin battery 404 is fitted to the wiring board 40 (i.e., inserted into the battery holder 95 mounted on the wiring substrate 40).

Step (4) The flexible substrate 50 side of the body temperature measuring unit 15 (the wiring substrate 40, the thermal resistor layer 30, the flexible substrate 50) is fixed to a central portion of the lower exterior body 20 in a close contact manner by a double-sided adhesive tape.

Step (5) One surface of the lining member 80 is stuck to the back surface (rear surface) of the upper exterior body 10 by a double-sided adhesive tape, and the buffer member 90 is stuck to the other surface of the lining member 80 by a double-sided adhesive tape.

Step (6) A peripheral edge portion of the upper exterior body 10 to which the lining member 80 and the buffer member 90 have been stuck and a peripheral edge portion of the lower exterior body 20 to which the body temperature measuring unit 15 has been fixed are fixed to each other in a close contact manner by a double-sided adhesive tape.

Step (7) The sticking member 60 is stuck to the bottom surface of the lower exterior body 20. In this manner, the deep body thermometer 1 is assembled (manufactured). In the exemplary embodiment, since the first temperature sensor 701 and the third temperature sensor 703 are not arranged at symmetrical positions with respect to the center of the lower exterior body 20, a mark 20a indicating the sticking direction of the sticking member 60 is put on the lower exterior body 20. The first temperature sensor 701 and the third temperature sensor 703 may be arranged at the symmetrical positions with respect to the center of the lower exterior body 20 and the mark 20a indicating the sticking direction of the sticking member 60 may be eliminated.

When the deep body thermometer 1 assembled as described above is used, first, a separator (release paper) attached to the second adhesive layer 602 (double-sided adhesive tape) of the sticking member 60 is peeled off. Then, after the power supply switch 406 is pressed from an outer side portion of the upper exterior body 10 to turn ON the power supply, the deep body thermometer 1 is stuck to a measurement site of the user (subject). Since the power supply switch 406 may be erroneously pressed during the measurement, it is preferable that an operation of turning ON/OFF the power supply be received by, for example, a long pressing operation of equal to or more than several seconds or by a plurality of pressing operations. When the operation is received, the LED 405 emits light in a predetermined light emission pattern to inform the user that the operation has been received. When the power supply is turned ON, the deep body temperature measurement, storage of the measurement data in the memory, and wireless data output are started. When the deep body temperature is measured, a measurement site is preferably the chest, the armpit, the back, the waist, the neck, back of the head, or the forehead. However, when body temperature fluctuation is measured, the measurement site may be the abdomen, the flank, the thigh, the ankle, the arm, the wrist, or the like.

As described in detail above, according to the exemplary embodiment, the peripheral edge portion of the upper exterior body 10 that is made of the foamed material of the closed cells or the semi-closed cells having waterproof properties and has flexibility and the peripheral edge portion of the lower exterior body 20 are made close contact with each other, the wiring substrate (electronic circuit) 40 is accommodated therein (in the accommodation space defined by the upper exterior body and the lower exterior body), and further, the sticking member 60 is stuck to the lower exterior body 20. With this configuration, it is possible to stick the deep body thermometer 1 to the body surface of the living body and cause the deep body thermometer 1 to follow movement of the living body (body movement). Therefore, a good wearing feeling can be provided. The upper exterior body 10 includes the stress relieving portions 10a which extend in the direction intersecting with the direction in which the stress generated by the external force acts and are smoothly curved with respect to the direction in which the stress acts so as to relieve the stress. Therefore, the stress relieving portions 10a are deformed upon reception of the stress, so that the stress is relieved (absorbed), thereby suppressing generation of wrinkles. Further, even when the wrinkles are generated, the wrinkles are concentrated in the stress relieving portions 10a, whereby it is possible to prevent wrinkles from being formed in other portions. As a result, it is possible to suppress the generation of wrinkles without impairing the wearing feeling.

Also, according to the exemplary embodiment, since the stress relieving portions 10a are provided concentrically with the outer edge of the top surface of the upper exterior body 10 along the outer edge of the top surface in plan view, wrinkles on the top surface of the upper exterior body 10 can be effectively suppressed.

In particular, according to the exemplary embodiment, since the stress relief portions 10a are provided concentrically with the outer edge of the lining member 80 in the outer side portion of the outer edge position of the lining member 80 in plan view, wrinkles that are generated at the boundary between the upper exterior body 10 and the lining member 80 can effectively be suppressed.

According to the embodiment, since the lining member 80 is stuck to and attached to the back surface (rear surface) of the upper exterior body 10, wrinkles are more difficult to be formed on the upper exterior body 10, and thus, the upper exterior body 10 can be tensioned.

Second Exemplary Embodiment

Figure 10:
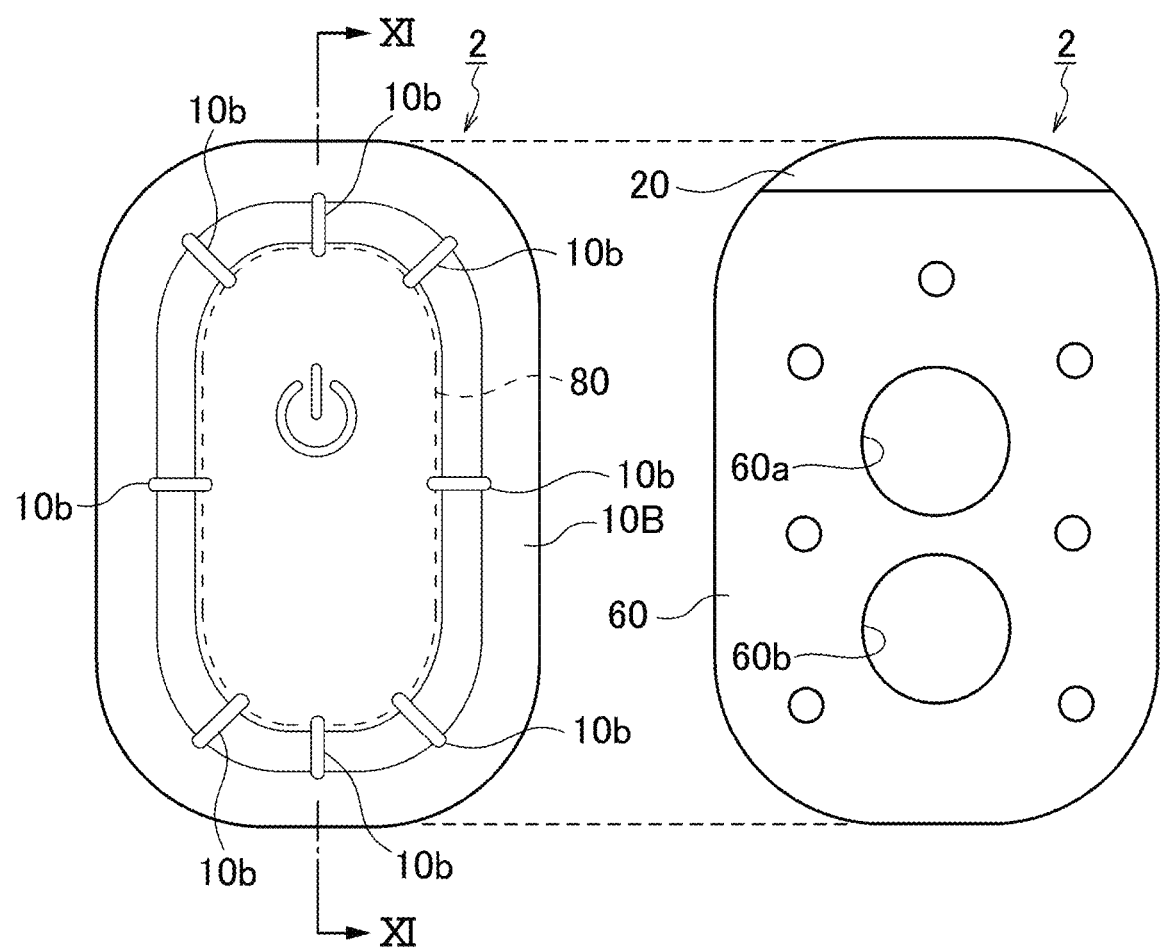
FIG. 10 includes a plan view and a bottom view illustrating an appearance of a deep body thermometer according to a second exemplary embodiment.
Figure 11:
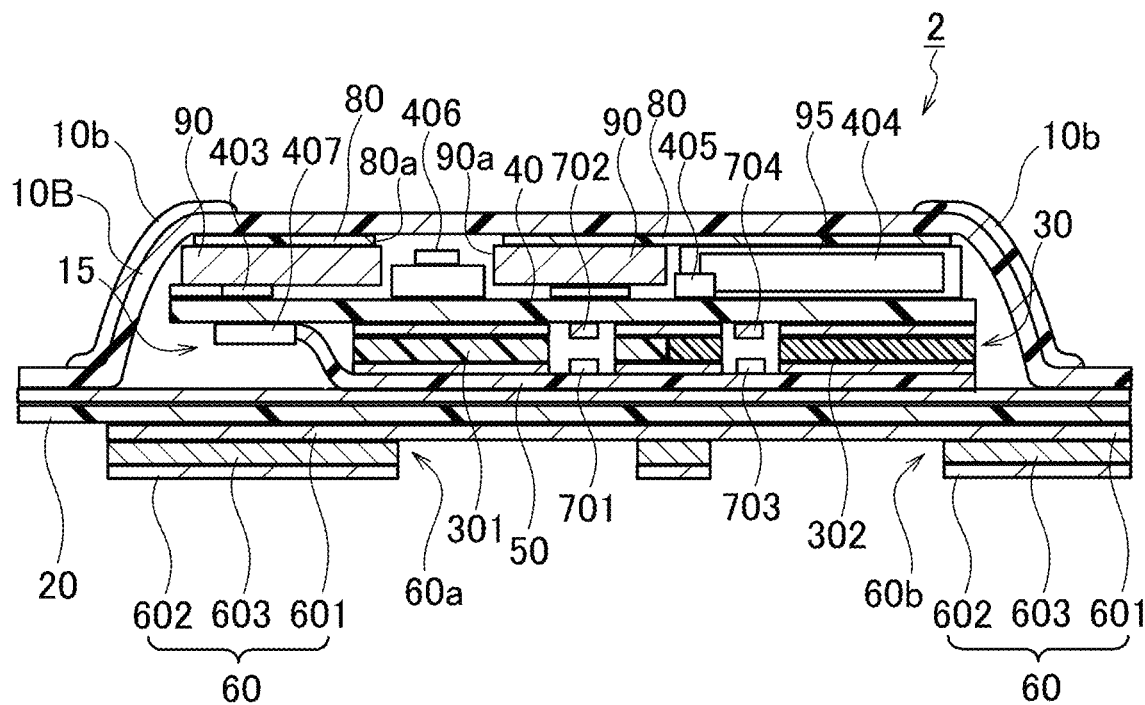
FIG. 11 is a cross-sectional view illustrating the configuration of the deep body thermometer according to the second exemplary embodiment.

Next, a deep body thermometer 2 according to a second embodiment will be described with reference to FIG. 10 and FIG. 11. Description of the same or similar configurations as or to those in the above-described first embodiment will be simplified or omitted and different points are mainly described. FIG. 10 includes a plan view and a bottom view illustrating the configuration of the deep body thermometer 2. FIG. 11 is a cross-sectional view illustrating the configuration of the deep body thermometer 2. It is noted that the same reference numerals denote components which are the same as or equivalent to those in the first embodiment in FIGS. 10 and 11.

The deep body thermometer 2 is different from the above-described deep body thermometer 1 in that the reinforcing portions (reinforcing ribs) 10b are provided instead of the stress relieving portions 10a.

That is, an upper exterior body 10B includes the reinforcing portions (reinforcing ribs) 10b that extend substantially in parallel to the direction in which stress generated by external force applied from the outside acts and are formed in substantially stripe-like shapes so as to resist the stress.

More specifically, the reinforcing portions 10b are provided on a side surface portion of the upper exterior body 10B so as to extend from an outer edge portion of a top surface (corresponding to a top surface portion) of the upper exterior body 10B to a flange portion (corresponding to a bottom portion) thereof and extend radially from the outer edge portion of the top surface of the upper exterior body 10B in plan view.

In particular, it is preferable that the reinforcing portions 10b be provided on the side surface portion (corresponding to a coupling portion) of the upper exterior body 10B so as to extend from positions on the outer edge of the lining member 80 to the flange portion (flange) and extend radially from the outer edge of the lining member 80 in plan view.

In the exemplary embodiment, as illustrated in FIG. 10, eight reinforcing portions 10b in total are provided at the four corners of the upper exterior body 10B and at the center portions of the respective sides. It is preferable that the reinforcing portions 10b be formed to have cross sections (cross sections cut by planes perpendicular to the extending directions) of substantially smooth semicircular shapes (or substantially circular arc shapes) in order to prevent the clothes or the like from being caught thereby.

According to the embodiment, the upper exterior body 10B includes the reinforcing portions (reinforcing ribs) 10b that extend substantially in parallel to the direction in which the stress generated by the external force acts and are formed in the substantially stripe-like shapes so as to resist the stress. Therefore, the reinforcing portions 10b suppress (reduce) deformation of the upper exterior body against the stress, thereby suppressing generation of wrinkles. As a result, it is possible to suppress the generation of wrinkles without impairing the wearing feeling.

According to the embodiment, since the reinforcing portions 10b are provided on the side surface portion of the upper exterior body 10B so as to extend from the outer edge portion of the top surface of the upper exterior body 10B to the flange portion (flange) and extend radially from the outer edge portion of the top surface of the upper exterior body 10B in plan view, wrinkles on the top surface of the upper exterior body 10B can be effectively suppressed.

In particular, according to the embodiment, since the reinforcing portions 10b are provided on the side surface portion of the upper exterior body 10B so as to extend from the positions on the outer edge of the lining member 80 to the flange portion and extend radially from the outer edge of the lining member 80 in plan view, wrinkles which are generated at the boundary between the upper exterior body 10B and the lining member 80 can be effectively suppressed.

Further, by forming the reinforcing portions 10b to have the cross sections of the substantially semicircular shapes, a contact area between the clothes or the like and the upper exterior body 10B is reduced when the upper exterior body 10B makes contact with the clothes or the like. As a result, friction is reduced and catching of clothes or the like can be reduced. In particular, by forming the reinforcing portions 10b along the inclined direction of the side surface, it is possible to suppress the deformation of the upper exterior body 10B and to reduce the catching of the clothes or the like.

While the exemplary embodiments of the invention have been described above, it should be appreciated that the invention is not limited to the embodiments described above, and various variations can be made. For example, in the above embodiments, the invention is applied to the two-heat flux-type deep body thermometer as the example for description, but the invention may be applied to a one-heat flux-type deep body thermometer. The invention can also be applied to a thermometer other than the deep body thermometer. Further, the invention can also be applied to, for example, an electrocardiograph and a sticking-type device for a living body, which measures respiration and pulses.

Figure 12A:
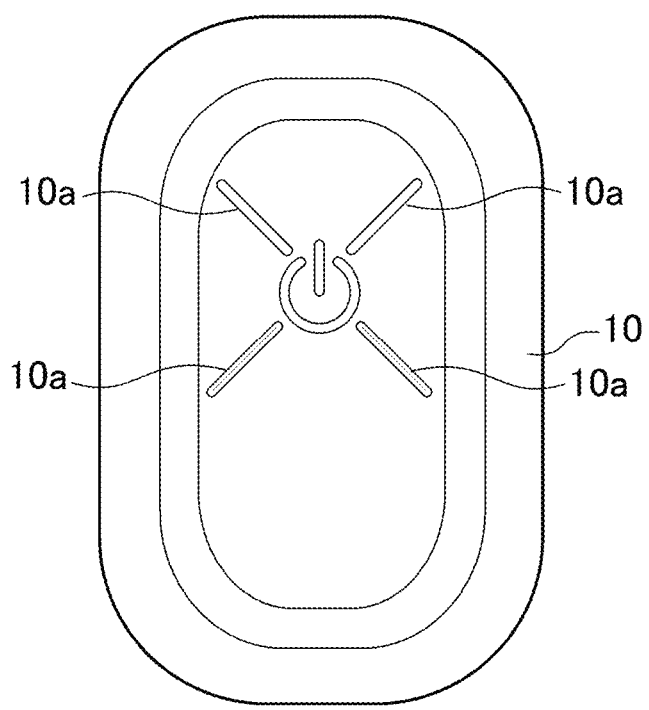
FIGS. 12A and 12B are plan views illustrating an appearance of a deep body thermometer according to a variation.
Figure 12B:
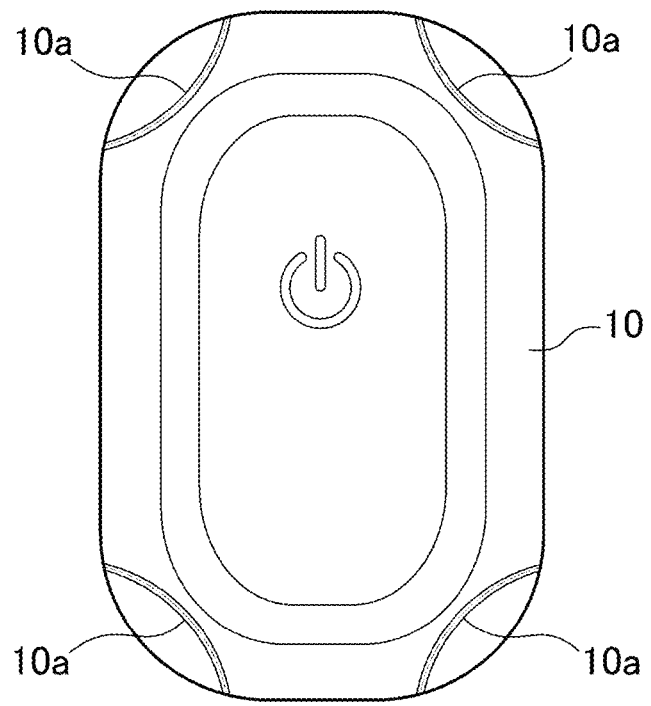

The shape, size, number, arrangement, and the like of the stress relieving portions 10a are not limited to those described in the above embodiment. Similarly, the shape, the size, the number, arrangement, and the like of the reinforcing portions 10b are not limited to those described in the above embodiment. For example, as illustrated in FIGS. 12A and 12B, the stress relieving portions 10a may be provided in the vicinity of corner portions (see FIG. 12A) of the flange portion (flange) of the upper exterior body 10 or in peripheral portions of the power supply switch 406 (see FIG. 12B).

Although the stress relieving portions 10a are provided in the first embodiment and the reinforcement portions 10b are provided in the second embodiment, both of the stress relieving portions 10a and the reinforcement portions 10b may be combined.

The shapes, sizes, and arrangement of the thermal resistor layer 30 (the first thermal resistor 301 and the second thermal resistor 302), the wiring substrate 40, the flexible substrate 50, the liner member 80, the buffer member 90 described above and the arrangement and the like of the first temperature sensor 701 to the fourth temperature sensor 704 are not limited to those in the above embodiments, and can be desirably set in accordance with requirements such as accuracy, for example. For example, the lining member 80 may be formed in a substantially tray-like shape and may be stuck so as to extend around the inner side surface of the upper exterior body 10. Moreover, the through-hole 90a of the buffer member 90 is not necessarily formed and may not be formed. In the above embodiments, the calculation of the deep body temperature is performed by the arithmetic processing circuit. Alternatively, the calculation of the deep body temperature may be performed by, for example, an external management device or an information terminal (for example, a smart phone or the like).

While exemplary embodiments of the invention have been described above, it is to be understood that variations and modifications will be apparent to those skilled in the art without departing from the scope and spirit of the invention. The scope of the invention, therefore, is to be determined solely by the following claims.

What is claimed is:

1. A biological sensor for a living body comprising:
    an upper exterior body comprising a waterproof foamed material of closed cells or semi-closed cells and having a hat-like shape or a trapezoidal shape in a side view thereof;
    a lower exterior body having a peripheral edge contacting the upper exterior body;
    an adhesive sticking member with a surface adhered to an outer side surface of the lower exterior body; and
    an electronic circuit accommodated in a space defined between the upper exterior body and the lower exterior body,
    wherein the upper exterior body includes a stress relieving portion that extends in a direction that intersects with a direction in which stress generated by an external force acts and that is smoothly curved with respect to the direction in which the stress acts so as to relieve the stress generated by the external force.

2. The biological sensor for the living body according to claim 1, wherein the stress relieving portion is provided concentrically with an outer edge of a top surface of the upper exterior body along the outer edge of the top surface in a plan view thereof.

3. The biological sensor for the living body according to claim 1, further comprising: a lining member having a plate shape and disposed on a back surface of the upper exterior body, wherein the stress relieving portion is provided concentrically with an outer edge of the lining member in an outer side portion of an outer edge position of the lining member in a plan view thereof.

4. The biological sensor for the living body according to claim 1, wherein the upper exterior body further includes a reinforcing portion that extends in parallel to the direction in which the stress generated by the external force acts and comprises a stripe-like shape such that the reinforcing portion is configured to resist the stress generated by the external force.

5. The biological sensor for the living body according to claim 4, wherein the reinforcing portion is disposed on a side surface portion of the upper exterior body such that the reinforcing portion extends from an outer edge portion of a top surface of the upper exterior body to a bottom portion and extends radially from the outer edge portion of the top surface of the upper exterior body in a plan view thereof.

6. The biological sensor for the living body according to claim 3, wherein the upper exterior body further includes a reinforcing portion that extends in parallel to the direction in which the stress generated by the external force acts and comprises a stripe-like shape with respect to the direction in which the stress acts such that the reinforcing portion is configured to resist the stress generated by the external force, and wherein the reinforcing portion is disposed on a side surface portion of the upper exterior body to extend from a position on the outer edge of the lining member to a bottom portion and extend radially from the position on the outer edge of the lining member in a plan view thereof.

7. The biological sensor for the living body according to claim 1, wherein the electronic circuit includes an operation switch that opposes a back surface of the upper exterior body and is configured to receive an operation by a user.

8. The biological sensor for the living body according to claim 1, wherein the electronic circuit includes a biological sensor configured to detect a biological signal from the living body.

9. The biological sensor for the living body according to claim 8, wherein the biological sensor is a temperature sensor configured to detect a temperature of the living body.

10. A biological sensor for a living body comprising:
an upper exterior body comprising a waterproof foamed material of closed cells or semi-closed cells and having a hat-like shape or a trapezoidal shape in a side view thereof;
a lower exterior body having a peripheral edge contacting the upper exterior body;
an adhesive sticking member with a surface adhered to an outer side surface of the lower exterior body; and
an electronic circuit accommodated in a space defined between the upper exterior body and the lower exterior body,
wherein the upper exterior body includes a reinforcing portion that extends in parallel to a direction in which stress generated by an external force acts and that includes a stripe-like shape configured to resist the stress generated by the external force.

11. The biological sensor for the living body according to claim 10, wherein the reinforcing portion is disposed on a side surface portion of the upper exterior body and extends from an outer edge portion of a top surface of the upper exterior body to a bottom portion and extends radially from the outer edge portion of the top surface of the upper exterior body in a plan view thereof.

12. The biological sensor for the living body according to claim 10, further including: a lining member having a plate shape and disposed on a back surface of the upper exterior body, wherein the reinforcing portion is disposed on a side surface portion of the upper exterior body and extends from a position on an outer edge of the lining member to a bottom portion and extends radially from the position on the outer edge of the lining member in a plan view thereof.

13. A biological sensor for a living body comprising:
an upper exterior body comprising a waterproof foamed material of closed cells or semi-closed cells and that is configured by a top surface, a bottom, and a coupling member that couples the top surface and the bottom;
a lower exterior body having a peripheral edge contacting the bottom of the upper exterior body;
an adhesive sticking member with a surface adhered to an outer side surface of the lower exterior body;
an electronic circuit accommodated in a space defined between the upper exterior body and the lower exterior body; and
a lining member that is mounted on the top surface of the upper exterior body in the space,
wherein the upper exterior body includes a projecting member or a recess that extends in a direction intersecting with a direction in which stress generated by an external force acts and is smoothly curved with respect to the direction in which the stress acts to relieve the stress at a position overlapping with neither an outer edge of the bottom nor the lining member in a plan view thereof.

14. The biological sensor for the living body according to claim 13, wherein the projecting member or the recess is provided concentrically with an outer edge of the top surface of the upper exterior body along the outer edge of the top surface in a plan view thereof.

15. The biological sensor for the living body according to claim 13, wherein the projecting member or the recess is provided concentrically with an outer edge of the lining member in an outer side portion of an outer edge position of the lining member in a plan view thereof.

16. The biological sensor for the living body according to claim 13, wherein the upper exterior body further includes a reinforcing portion that extends in parallel to the direction in which the stress generated by the external force acts such that the reinforcing portion is configured to resist the stress generated by the external force.

17. The biological sensor for the living body according to claim 16, wherein the reinforcing portion is disposed on the coupling member of the upper exterior body and extends from an outer edge of the top surface of the upper exterior body to the bottom and further extends radially from the outer edge of the top surface of the upper exterior body in a plan view thereof.

18. A biological sensor for a living body comprising:
an upper exterior body comprising a waterproof foamed material of closed cells or semi-closed cells and that is configured by a top surface, a bottom, and a coupling member that couples the top surface to the bottom;
a lower exterior body having a peripheral edge contacting the bottom of the upper exterior body;
an adhesive sticking member with a surface adhered to an outer side surface of the lower exterior body;
an electronic circuit accommodated in a space defined between the upper exterior body and the lower exterior body; and
a lining member coupled to the top surface of the upper exterior body in the space, wherein the upper exterior body includes a reinforcing portion that extends in parallel to a direction in which stress generated by an external force acts and includes a stripe-like shape configured to resist the stress at a position overlapping with neither an outer edge of the bottom nor the lining member in a plan view thereof.

19. The biological sensor for the living body according to claim 18, wherein the reinforcing portion is disposed on the coupling member of the upper exterior body and extends from an outer edge of the top surface of the upper exterior body to the bottom and further extends radially from the outer edge of the top surface of the upper exterior body in a plan view thereof.

20. The biological sensor for the living body according to claim 18, wherein the reinforcing portion is disposed on the coupling member of the upper exterior body and extends from a position on an outer edge of the lining member to the bottom and further extends radially from the position on the outer edge of the lining member in a plan view thereof.

* * * * *